(12) United States Patent
Allen et al.

(10) Patent No.: US 9,249,374 B2
(45) Date of Patent: Feb. 2, 2016

(54) LIGHT-DUTY LIQUID DETERGENTS BASED ON COMPOSITIONS DERIVED FROM NATURAL OIL METATHESIS

(75) Inventors: Dave R Allen, Chicago, IL (US); Randal J Bernhardt, Antioch, IL (US); Scott Dillavou, Skokie, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/880,026

(22) PCT Filed: Oct. 25, 2011

(86) PCT No.: PCT/US2011/057626
§ 371 (c)(1),
(2), (4) Date: May 13, 2013

(87) PCT Pub. No.: WO2012/061110
PCT Pub. Date: May 10, 2012

(65) Prior Publication Data
US 2013/0288946 A1    Oct. 31, 2013

Related U.S. Application Data

(60) Provisional application No. 61/406,556, filed on Oct. 25, 2010, provisional application No. 61/406,547, filed on Oct. 25, 2010, provisional application No. 61/406,570, filed on Oct. 25, 2010.

(51) Int. Cl.

| | | |
|---|---|---|
| *C11C 3/08* | (2006.01) |
| *A01N 25/02* | (2006.01) |
| *A01N 25/04* | (2006.01) |
| *A01N 25/30* | (2006.01) |
| *A01N 33/12* | (2006.01) |
| *A01N 37/18* | (2006.01) |
| *A01N 37/44* | (2006.01) |
| *A01N 41/04* | (2006.01) |
| *A61K 8/41* | (2006.01) |
| *A61K 8/42* | (2006.01) |
| *A61K 8/44* | (2006.01) |
| *A61K 8/46* | (2006.01) |
| *A61K 8/92* | (2006.01) |
| *A61Q 5/12* | (2006.01) |
| *A61Q 19/10* | (2006.01) |
| *A62D 1/02* | (2006.01) |
| *B01F 17/00* | (2006.01) |
| *C07C 69/533* | (2006.01) |
| *C07C 69/593* | (2006.01) |
| *C07C 209/12* | (2006.01) |

(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C09K 8/00* (2013.01); *C09K 15/28* (2013.01); *C11C 3/00* (2013.01); *C11C 3/003* (2013.01); *C11D 1/002* (2013.01); *C11D 1/04* (2013.01); *C11D 1/28* (2013.01); *C11D 1/62* (2013.01); *C11D 1/652* (2013.01); *C11D 1/74* (2013.01); *C11D 1/83* (2013.01); *C11D 1/90* (2013.01); *C11D 1/92* (2013.01); *C11D 1/94* (2013.01); *C11D 3/48* (2013.01); *C08K 5/20* (2013.01); *C08K 5/32* (2013.01); *C08K 5/41* (2013.01)

(58) Field of Classification Search
None
See application file for complete search history.

(56) References Cited

U.S. PATENT DOCUMENTS

| | | |
|---|---|---|
| 2,653,970 A | 9/1953 | Fessler et al. |
| 3,169,142 A | 2/1965 | Knaggs et al. |

(Continued)

FOREIGN PATENT DOCUMENTS

| | | |
|---|---|---|
| EP | 0699228 | 12/1996 |
| EP | 2004786 | 10/2010 |
| WO | WO-9836041 | 8/1998 |
| WO | WO-0119507 | 3/2001 |
| WO | WO-2008048522 | 4/2008 |
| WO | WO-2011075642 | 6/2011 |
| WO | WO-2012061110 | 5/2012 |

OTHER PUBLICATIONS

Tetrahedron 68 2012 , 1117.
Appl. Catal.A. 346 2009 , 158.
J.C. Mol., Topics in Catalysis 27 2004 , 97.
J. C. Mol., Green Chem., 4 2002 , 5.

*Primary Examiner* — Necholus Ogden, Jr.
(74) *Attorney, Agent, or Firm* — Dilworth IP LLC

(57) ABSTRACT

Light-duty liquid detergents derived from metathesized natural oil feedstocks are disclosed. The detergents comprise water, at least one anionic surfactant, and at least one secondary surfactant derived from a metathesis-derived $C_{10}$-$C_{17}$ monounsaturated acid or its ester derivatives. In particular, the secondary surfactant is selected from $C_{10}$ amidoamines, quaternized $C_{10}$ or $C_{12}$ amidoamines, $C_{12}$ amidoamine oxides, $C_{12}$ sulfobetaines, $C_{12}$ amidoamine sulfobetaines, and $C_{12}$ alkanolamides. The detergents noted above rival or outperform commercial baselines in standard foam tests for liquid detergents, particularly those used for dishwashing.

10 Claims, No Drawings

(51) Int. Cl.

| | |
|---|---|
| *C07C 211/21* | (2006.01) |
| *C07C 219/08* | (2006.01) |
| *C07C 231/12* | (2006.01) |
| *C07C 237/16* | (2006.01) |
| *C07C 303/18* | (2006.01) |
| *C08G 65/26* | (2006.01) |
| *C08K 5/01* | (2006.01) |
| *C09K 8/00* | (2006.01) |
| *C09K 15/28* | (2006.01) |
| *C11C 3/00* | (2006.01) |
| *C11D 1/00* | (2006.01) |
| *C11D 1/04* | (2006.01) |
| *C11D 1/28* | (2006.01) |
| *C11D 1/62* | (2006.01) |
| *C11D 1/65* | (2006.01) |
| *C11D 1/74* | (2006.01) |
| *C11D 1/83* | (2006.01) |
| *C11D 1/90* | (2006.01) |
| *C11D 1/92* | (2006.01) |
| *C11D 1/94* | (2006.01) |
| *C11D 3/48* | (2006.01) |
| *C08K 5/20* | (2006.01) |
| *C08K 5/32* | (2006.01) |
| *C08K 5/41* | (2006.01) |

(56) References Cited

U.S. PATENT DOCUMENTS

| | | | |
|---|---|---|---|
| 3,544,613 A | 12/1970 | Knaggs et al. | |
| 3,929,678 A | 12/1975 | Laughlin et al. | |
| 4,087,457 A | 5/1978 | Convers et al. | |
| 4,148,821 A | 4/1979 | Nussbaum et al. | |
| 4,275,013 A | 6/1981 | Tokosh et al. | |
| 4,451,385 A | 5/1984 | Tavss et al. | |
| 4,545,941 A | 10/1985 | Rosenburg | |
| 5,415,801 A | 5/1995 | Ofosu-Asante | |
| 5,478,500 A | 12/1995 | Swift et al. | |
| 5,482,908 A | 1/1996 | Le-khac | |
| 5,698,505 A | 12/1997 | Ofosu-Asante | |
| 5,712,241 A | 1/1998 | Gorlin et al. | |
| 5,814,590 A | 9/1998 | Sherry et al. | |
| 5,929,022 A | 7/1999 | Velazquez | |
| 5,939,378 A | 8/1999 | Stringer et al. | |
| 5,965,508 A | 10/1999 | Ospinal et al. | |
| 5,998,347 A | 12/1999 | D'Ambrogio et al. | |
| 6,127,328 A | 10/2000 | D'Ambrogio et al. | |
| 6,281,178 B1 | 8/2001 | Ryklin et al. | |
| 6,284,723 B1 | 9/2001 | Zhou et al. | |
| 6,365,561 B1 | 4/2002 | Vinson et al. | |
| 6,387,860 B1 | 5/2002 | Gambogi et al. | |
| 6,399,553 B1 | 6/2002 | Cable et al. | |
| 6,489,285 B2 | 12/2002 | Faber | |
| 6,511,953 B1 | 1/2003 | Fontana et al. | |
| 6,528,477 B2 | 3/2003 | Kasturi et al. | |
| 6,605,584 B2 | 8/2003 | Fong et al. | |
| 6,660,706 B1 | 12/2003 | Koester et al. | |
| 6,949,498 B2 | 9/2005 | Murphy et al. | |
| 7,169,745 B2 | 1/2007 | Kasturi et al. | |
| 7,576,227 B2 | 8/2009 | Bicerano et al. | |
| 7,608,573 B1 | 10/2009 | Scheuing | |
| 7,884,064 B2 | 2/2011 | Bernhardt et al. | |
| 7,960,599 B2 | 6/2011 | Millis et al. | |
| 8,067,610 B2 | 11/2011 | Schrodi | |
| 8,247,362 B2 | 8/2012 | Murphy et al. | |
| 2002/0169099 A1 | 11/2002 | Knox et al. | |
| 2007/0010680 A1* | 1/2007 | Yajima et al. | 554/51 |
| 2007/0167332 A1 | 7/2007 | Subramamian et al. | |
| 2008/0033026 A1 | 2/2008 | Zullo et al. | |
| 2009/0264672 A1 | 10/2009 | Abraham et al. | |
| 2010/0145086 A1 | 6/2010 | Schrodi et al. | |
| 2010/0184855 A1 | 7/2010 | Bernhardt et al. | |
| 2010/0197554 A1 | 8/2010 | Koyuncu et al. | |
| 2010/0282467 A1 | 11/2010 | Hutchison et al. | |
| 2010/0323942 A1 | 12/2010 | Evers et al. | |
| 2011/0113679 A1 | 5/2011 | Cohen et al. | |
| 2011/0313180 A1 | 12/2011 | Uptain et al. | |
| 2012/0071676 A1 | 3/2012 | Schrodi et al. | |
| 2012/0197031 A1 | 8/2012 | Firth et al. | |
| 2013/0035502 A1 | 2/2013 | Cohen et al. | |
| 2013/0035532 A1 | 2/2013 | Schrodi | |

* cited by examiner

LIGHT-DUTY LIQUID DETERGENTS BASED ON COMPOSITIONS DERIVED FROM NATURAL OIL METATHESIS

FIELD OF THE INVENTION

The invention relates to light-duty liquid detergents, and particularly to compositions useful therein as surfactants that derive from natural oil metathesis.

BACKGROUND OF THE INVENTION

Light-duty liquid ("LDL") detergents are commonly used in hand dishwashing liquids, shampoos, cleaners, and some laundry applications. The detergents are aqueous formulations that usually include an anionic surfactant, which is the principal suds producer, along with a secondary surfactant.

Because anionic surfactants tend to irritate skin and cause chapping, formulations that omit anionic surfactants (see, e.g., U.S. Pat. Appl. Publ. No. 2002/0169099) or include proteases, humectants, or other additives to counteract their undesirable effects (see, e.g., U.S. Pat. No. 4,451,385 and U.S. Pat. Appl. Publ. No. 2010/0197554) have been developed.

More often, however, anionic surfactants (typically, one or more of a linear alkylbenzene sulfonate, a fatty alcohol sulfate, or a fatty alcohol ether sulfate) are the primary surfactant components, and one challenge is to identify suitable secondary surfactants that can be used with the primary surfactant(s). Ideally, the secondary surfactant maintains or enhances sudsing performance and allows a reduced amount of anionic surfactant to be used. U.S. Pat. No. 7,884,064, for instance, teaches dish detergent formulations comprising sulfonated estolides (anionic surfactant) in combination with a fatty amine oxide, betaine, sulfobetaine, or alkanolamide as the secondary surfactant.

Occasionally, light-duty liquid detergents have been formulated to contain fatty esters or amides made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. These materials are generally less than completely satisfactory, however, because compounds having such large carbon chains can behave functionally as soil under some washing conditions.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, surfactants have generally not been made from these feedstocks.

We recently described new compositions made from feedstocks based on self-metathesis of natural oils or cross-metathesis of natural oils and olefins. In particular, we identified esteramines and ester quats, fatty amides, fatty amines and amidoamines, quaternized amines, betaines, sulfobetaines, alkoxylates, sulfonates, sulfo-estolides, and other compositions made by derivatizing the unique feedstocks (see copending PCT/US11/57596, PCT/US11/57597, PCT/US11/57595, PCT/US11/57602, PCT/US11/57605, and PCT/US11/57609, all filed Oct. 25, 2011. The feedstocks, which include $C_{10}$-$C_{17}$ monounsaturated acids and their ester derivatives, preferably have at least 1 mole % of trans-$\Delta^9$ unsaturation. Because performance of a particular surfactant or blend of surfactants in a light-duty liquid detergent is not easily inferred from surfactant structure, we performed extensive experimental investigations to identify subclasses of surfactants having desirable attributes for use in LDL detergents.

New surfactant classes are always of interest to formulators of light-duty liquid detergents. Surfactants based on renewable resources will continue to be in demand as alternatives to petroleum-based surfactants. Traditional natural sources of fatty acids and esters used for making surfactants generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). Formulators will benefit from identification of particular subclasses of surfactants that derive from renewable sources and have desirable attributes for LDL detergents.

SUMMARY OF THE INVENTION

The invention relates to light-duty liquid detergents. The detergents comprise water, at least one anionic surfactant, and at least one secondary surfactant. The secondary surfactant is derived from a metathesis-derived $C_{10}$-$C_{17}$ monounsaturated acid or its ester derivatives. In particular, the secondary surfactant is selected from $C_{10}$ amidoamines, quaternized $C_{10}$ or $C_{12}$ amidoamines, $C_{12}$ amidoamine oxides, $C_{12}$ sulfobetaines, $C_{12}$ amidoamine sulfobetaines, and $C_{12}$ alkanolamides.

We surprisingly found that replacement of secondary surfactants used in conventional light-duty liquid detergent formulations with the metathesis-derived compositions noted above imparts equal or better foaming performance versus control formulations.

DETAILED DESCRIPTION OF THE INVENTION

Light-duty liquid detergents of the invention comprise water, an anionic surfactant, and at least one secondary surfactant derived from metathesis of a natural oil.

The amount of water used is typically in the range of 50 to 99 wt. %, preferably from 60 to 98 wt. %, and more preferably from 70 to 96 wt. %. However, the LDL detergent may be supplied or sold as a concentrate that contains the minimum amount of water needed to solubilize the components. The formulator or even the ultimate customer may dilute the concentrate with water for normal use.

At least one anionic surfactant is included. Anionic surfactants generally have a molecular weight below 10,000 and comprise one or more functional groups that exhibit a net anionic charge when in aqueous solution. Suitable anionic surfactants include fatty alkyl sulfates, fatty alkyl ether sulfates, paraffin sulfonates, olefin sulfonates, alkyl aryl sulfonates, alkyl ester sulfonates, fatty ester sulfonates, sulfosuccinate esters, organic phosphates, alkyl alkoxylated sulfates, sulfonated estolides, and the like. Additional examples of suitable anionic surfactants are described in U.S. Pat. Nos. 3,929,678, 5,698,505, 5,929,022, 6,399,553, 6,489,285, 6,511,953, 6,949,498, 7,884,064, and U.S. Pat. Appl. Publ. No. 2010/0184855, the teachings of which are incorporated herein by reference.

The amount of anionic surfactant (based on active material) used is typically within the range of 0.1 to 30 wt. %, preferably from 0.2 to 20 wt. %. If desired, an anionic surfactant derived from natural oil metathesis can be used in addition to or instead of a conventional anionic surfactant.

The inventive LDL detergents include at least one secondary surfactant that is derived from metathesis of a natural oil. Through extensive experimentation, we identified particular classes of such compositions that perform as well as or better than commercial secondary surfactants in light-duty liquid detergent formulations. Thus, suitable secondary surfactants derive from a metathesis-derived $C_{10}$-$C_{17}$ monounsaturated acid or its ester derivatives and are selected from $C_{10}$ amidoamines, quaternized $C_{10}$ or $C_{12}$ amidoamines, $C_{12}$ amidoamine oxides, $C_{12}$ sulfobetaines, $C_{12}$ amidoamine sulfobetaines, and $C_{12}$ alkanolamides.

The amount of secondary surfactant used is typically within the range of 0.1 to 10 wt. %, preferably from 0.2 to 8 wt. %, and more preferably from 0.3 to 6 wt. %.

As the examples below demonstrate, the light-duty liquid detergents identified above rival or outperform commercial baselines in standard foam tests for liquid detergents, particularly those used for dishwashing. In particular, when the usual fatty amine oxide is replaced with an inventive surfactant in an LDL formulation that utilizes a linear alkylbenzene sulfonate or fatty alcohol ether sulfate as the anionic surfactant, good foaming performance is achieved. We found that only certain subclasses of tested compositions performed as well as or better than the control (see Tables 3 and 4) in a standard foaming test, while other compositions, often structurally similar, performed poorly in the test (see Table 5).

The $C_{10}$-$C_{17}$ monounsaturated acid or its ester derivative used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived surfactants used in the inventive LDL detergents, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to surfactant compositions made from them, including, for example, modified physical form, melting range, compactability, and other important properties. These differences should allow formulators that use surfactants greater latitude or expanded choice as they use them in cleaners, fabric treatment, personal care, agricultural uses, and other end uses, particularly LDL detergents.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized, the alkyl ester mixture will include a $C_{18}$ unsaturated diester. When the natural oil is cross-metathesized with an α-olefin, the alkyl ester mixture includes a $C_{10}$ unsaturated alkyl ester and one or more $C_{11}$ to $C_{17}$ unsaturated alkyl ester coproducts. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making surfactants for the inventive LDL detergents.

Natural oils suitable for use as a feedstock to generate the $C_{10}$-$C_{17}$ monounsaturated acid or its ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty acid residues derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to secondary surfactant compositions for the light-duty liquid detergents.

An alternative to using a natural oil as a feedstock to generate the $C_{10}$-$C_{17}$ monounsaturated acid or its ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb); or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

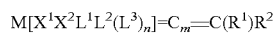

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

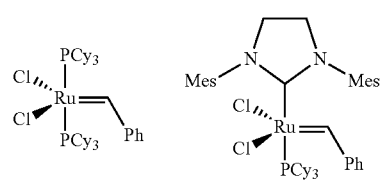

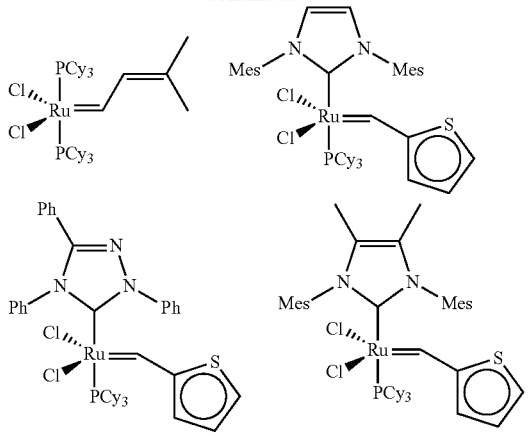

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The metathesis-derived $C_{10}$-$C_{17}$ monounsaturated acid or its ester derivatives are converted to particular subclasses of amidoamines, quaternized amidoamines, amidoamine oxides, amidoamine sulfobetaines, alkanolamides, and other compositions that are useful as secondary surfactants in light-duty liquid detergents. General synthetic procedures for making these compositions are provided below (General procedures C-J) and are summarized for each particular composition prepared in Table 2. For instance, quaternized amidoamine sulfonate C10-18 is conveniently made using Methods E and C by reacting methyl 9-decenoate with dimethylaminopropyl amine to make the DMAPA amide, followed by quaternization of the tertiary amine group with dimethyl sulfate.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

As used herein, "low-EO" alkoxylates have an average of 0.5 to 5 EO units, "mid-EO" alkoxylates have an average of 5 to 15 EO units, and "high-EO" alkoxylates have an average of 15 to 50 EO units.

In some preferred LDL detergents, the secondary surfactant is a $C_{10}$ amidoamine. An exemplary $C_{10}$ amidoamine is conveniently made by reacting methyl 9-decenoate (obtained from metathesis of a natural oil) with DMAPA and has the structure:

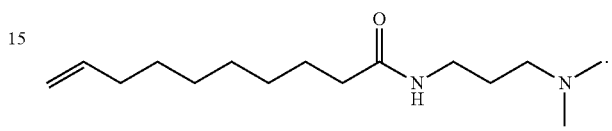

In other preferred LDL detergents, the secondary surfactant is a quaternized $C_{10}$ or $C_{12}$ amidoamine. Exemplary quaternized amidoamines are conveniently made by reacting methyl 9-decenoate or methyl 9-dodecenoate with DMAPA, followed by quaternization with dimethyl sulfate, methyl chloride, or other suitable quaternizing agents. Examples include:

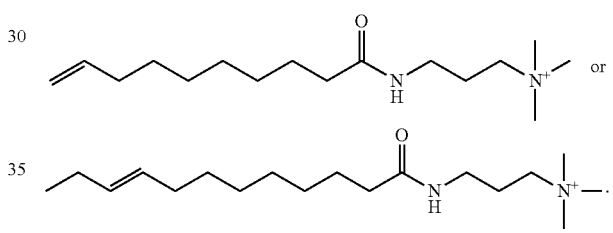

In other preferred LDL detergents, the secondary surfactant is a $C_{12}$ amidoamine oxide. Exemplary amidoamine oxides are made by reacting the amidoamines described above with hydrogen peroxide or other suitable oxidants to give the amine oxide. One preferred example:

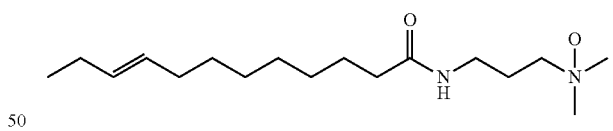

In other preferred LDL detergents, the secondary surfactant is a $C_{12}$ amidoamine sulfobetaine. Exemplary amidoamine sulfobetaines are made by reacting the amidoamines described above with the reaction product of epichlorohydrin and sodium metabisulfite. A preferred example:

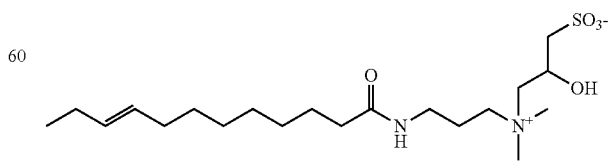

In other preferred LDL detergents, the secondary surfactant is a $C_{12}$ sulfobetaine. Exemplary sulfobetaines are made by reacting a fatty amine with the reaction product of epichlorohydrin and sodium metabisulfite. A preferred example:

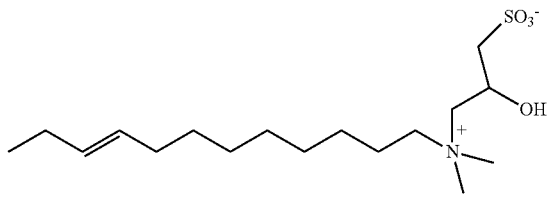

In other preferred LDL detergents, the secondary surfactant is a $C_{12}$ alkanolamide. Exemplary alkanolamides are made by reacting methyl 9-dodecenoate with an alkanolamine such as ethanolamine, isopropanolamine, or the like. Two examples:

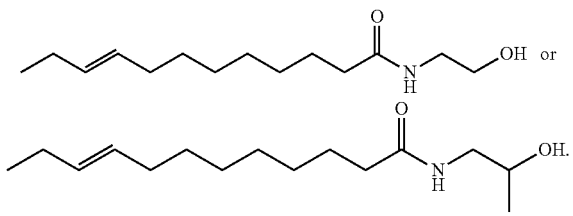

An organic solvent, preferably a water-soluble one, may be included in the LDL detergents. Preferred solvents include alcohols, glycols, glycol ethers, glycol ether esters, amides, esters, and the like. Examples include $C_1$-$C_6$ alcohols, $C_1$-$C_6$ diols, $C_3$-$C_{24}$ glycol ethers, and mixtures thereof. Suitable alcohols include, for example, methanol, ethanol, 1-propanol, isopropanol, 1-butanol, 1-pentanol, 1-hexanol, amyl alcohol, and mixtures thereof. Suitable glycol ethers include, e.g., ethylene glycol n-butyl ether, ethylene glycol n-propyl ether, propylene glycol methyl ether, propylene glycol n-propyl ether, propylene glycol tert-butyl ether, propylene glycol n-butyl ether, diethylene glycol n-butyl ether, dipropylene glycol methyl ether, and the like, and mixtures thereof. Suitable glycol ether esters include, for example, propylene glycol methyl ether acetate, propylene glycol n-butyl ether acetate, and the like. Other organic solvents suitable for use in LDL detergents are well known and have been described for example, in U.S. Pat. Nos. 5,814,590, 6,284,723, 6,399,553, and 6,605,584, and in U.S. Pat. Appl. Publ. No. 2010/0184855, the teachings of which are incorporated herein by reference.

The light-duty liquid detergents can include additional conventional surfactants, including nonionic and amphoteric or zwitterionic surfactants. Nonionic surfactants typically function as wetting agents, hydrotropes, and/or couplers. Suitable nonionic surfactants include, for example, fatty alcohols, alcohol fatty esters, fatty alcohol ethoxylates, alkylphenol ethoxylates, alkoxylate block copolymers, alkoxylated fatty amides, fatty amides, fatty amine oxides, castor oil alkoxylates, polyol esters, fatty methyl esters, glycerol esters, glycol fatty esters, tallow amine ethoxylates, polyethylene glycol esters, and the like. Fatty alcohol ethoxylates are preferred. Suitable amphoteric surfactants include, for example, amine oxides, betaines, sulfobetaines, and the like. Specific examples include cocoamidopropylamine oxide, cetamine oxide, lauramine oxide, myristylamine oxide, stearamine oxide, alkyl betaines, cocobetaines, and amidopropyl betaines, (e.g., lauryl betaines, cocoamidopropyl betaines, lauramidopropyl betaines), and combinations thereof. Other suitable nonionic and amphoteric surfactants are disclosed in U.S. Pat. Nos. 5,698,505, 5,814,590, 6,281,178, 6,284,723, 6,605,584, and 6,511,953, the teachings of which related to those surfactants are incorporated herein by reference.

The light-duty liquid detergent can include additional conventional components. Commonly, the detergents include one or more additives such as builders, buffers, abrasives, electrolytes, diamines, bleaching agents, fragrances, dyes, foaming control agents, foam enhancers, polymeric suds stabilizers, antimicrobial agents, thickeners, pigments, gloss enhancers, enzymes, dispersants, hydrotropes, opacifiers, chelants, preservatives, UV light absorbers, color stabilizers, vitamins, herbal extracts, emollients, skin conditioners, humectants, rheology modifiers, pearlescent agents, and the like. For specific examples, see U.S. Pat. Nos. 5,698,505, 6,365,561, 6,528,477, 7,169,745, and 7,884,064 and U.S. Pat. Appl. Publ. No. 2010/0197554, the teachings of which are incorporated herein by reference.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

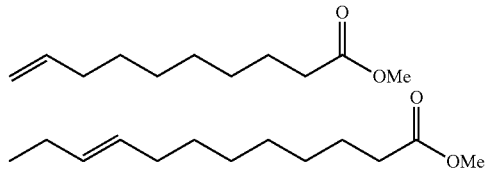

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 µtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/ mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |

TABLE 1-continued

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Quaternization: General Procedure C

Tertiary amines are converted to methyl quats, betaines, or sulfobetaines by reaction with a quaternizing agent. The quaternization is performed at temperature within the range of 65° C. to 100° C. The quaternizing agent used is dimethyl sulfate for methyl quats, sodium monochloroacetate for betaines, or epichlorohydrin for sulfobetaines. The amount of quaternizing agent used is from 0.8 to 1.0 molar equivalents based on the amount of tertiary amine. The reaction is deemed complete when the free amine value is in the desired range as determined by perchloric acid titration.

Amine Oxides from Amines: General Procedure D

A tertiary amine is diluted with water to form a 10-40 wt. % mixture, which is warmed to 50° C. to 75° C. under nitrogen. Hydrogen peroxide solution (35% solution, 1 to 2.2 molar eq.) is added dropwise while keeping the temperature below 75° C. The mixture is held at the reaction temperature for 4 to 12 h or until the free peroxide level is below 0.2% as determined by starch iodide paper.

Amide Synthesis (Including Amidoamines): General Procedure E

Unsaturated methyl ester ($C_{10}$, $C_{12}$, or $C_{16}$ monoester or $C_{18}$ diester) is combined with 1-6 molar equivalents of a primary or secondary amine (e.g., DMA, DEA, MEA, DMAPA). A base catalyst (e.g., NaOMe or other alkoxide) is added if desired. The reaction mixture is heated at a temperature within the range of 50° C. to 150° C. until the starting ester is substantially consumed. The amide product is purified by distillation, water washing, or other normal means. Alternatively, the product is used "as is" and converted to other derivatives.

Esterification to Make Ethoxylates (eFAMEs): General Procedure F

A suitable carboxylic acid is combined with a poly(ethylene glycol)monomethyl ether (0.8-2.5 eq.), an acid catalyst (e.g., sulfuric acid, methanesulfonic acid, p-toluenesulfonic acid, or the like), and optionally a solvent (e.g., toluene, xylene, or other hydrocarbons capable of forming a water azeotrope). The mixture is heated at 120° C. to 180° C. under vacuum, nitrogen sparge, or nitrogen blanket and the liberated water is collected. The reaction continues until the desired acid value is achieved.

Amines by Amide Reduction: General Procedure G

Lithium aluminum hydride (or a similar reducing agent) is dissolved in a solvent (e.g., diethyl ether, THF, dioxane, diglyme) under a nitrogen blanket. A suitable fatty amide is dissolved in the same solvent and is added dropwise, keeping the reaction temperature within the range of 25° C. to 50° C. After the addition, the mixture is stirred overnight at room temperature. Water is carefully added to quench the reaction, and aqueous sodium hydroxide is added. The solids are filtered off, and the solvent is removed. The amine product is purified by distillation.

Imidazoline Synthesis: General Procedure H

Methyl 9-decenoate or methyl 9-dodecenoate is combined with diethylenetriamine (DETA) or 2-(2-aminoethylamino) ethanol (AEEA), with or without a catalyst, in the desired molar ratio of ester groups to primary amino and/or hydroxyl groups. Usually, two moles of ester are used for each mole of DETA or AEEA. The mixture is heated with agitation to a temperature within the range of 140° C. and 200° C. under a mild vacuum that prevents or minimizes evaporation of DETA or AEEA from the reaction mixture. The reaction proceeds until analysis (IR or $^1$H NMR spectroscopy) indicates reasonably complete conversion. The contents are then heated at a temperature within the range of 175° C. to 300° C. with a lower vacuum (5-100 mm Hg) to effect ring closure to the imidazoline. Reaction end point is determined by titration.

Sulfitation of Olefins: General Procedure J

A sulfitating agent (sodium sulfite, sodium bisulfite, sodium metabisulfite, or the like) is dissolved in water and combined with at least a molar equivalent of an olefin. Optionally, a catalyst (peroxides, iron, or other free-radical initiators) is included. The mixture is heated to 50° C.-100° C. for 3-15 h until sulfitation is reasonably complete.

Table 2 summarizes the general procedures used to prepare the following compositions:

TABLE 2

General Methods Used to Synthesize Compositions

| Composition | Methods | Composition | Methods | Composition | Methods | Composition | Methods |
|---|---|---|---|---|---|---|---|
| C10-11 | F | C10-24 | E, C | C12-12 | H | C12-26* | E, G |
| C10-12 | H | C10-25 | E | C12-13 | H, C | C12-28 | E, G, D |
| C10-13 | H, C | C10-27 | E | C12-14 | H, C, J | C12-29 | E, J |
| C10-14 | H, C, J | C10-28 | E | C12-15 | H | C12-30* | E |
| C10-15 | H | C10-30 | F, J | C12-17* | E | C12-31 | E |
| C10-17* | E | C10-38 | E, G | C12-18* | E, C | C12-32 | F, J |
| C10-18* | E, C | C10-39 | E, G, D | C12-19 | E, C, J | C12-33 | F, J |
| C10-19 | E, C, J | C10-41 | E, G, C | C12-20* | E, D | C12-38 | E |
| C10-20 | E, D | C12-8 | F | C12-22 | E, C | C12-40 | E, G, C |
| C10-21 | E, D, J | C12-9 | F | C12-23 | E, C, J | C12-46* | E, G, C |
| C10-22 | E, C | C12-10 | F, J | C12-24* | E, C | | |
| C10-23 | E, C, J | C12-11 | F | C12-25* | E | | |

Methods: C: quaternization to methyl quat, betaine, or sulfobetaine; D: oxidation of amine to amine oxide; E: amide from unsaturated ester and primary or secondary amine; F: ethoxylated fatty acid methyl ester from unsaturated fatty acid; G: amine from amide by reduction; H: imidazoline preparation from unsaturated ester + DETA or AEEA; J: sulfitation of olefins.
*A detailed procedure for synthesizing this composition is included hereinbelow.

Each of the following compositions is tested as a surfactant component of a light-duty liquid detergent formulation. Unless otherwise indicated below, the compositions are prepared using the general methods summarized in Table 2:

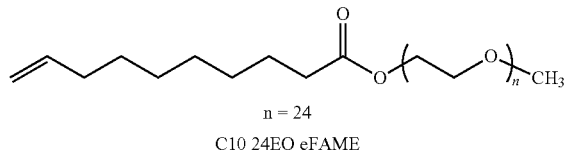
n = 24
C10 24EO eFAME

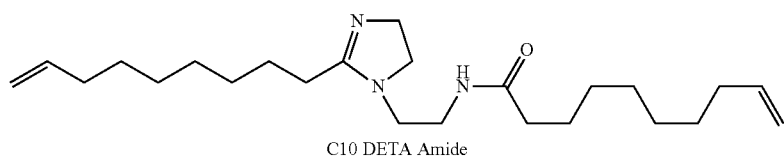
C10 DETA Amide

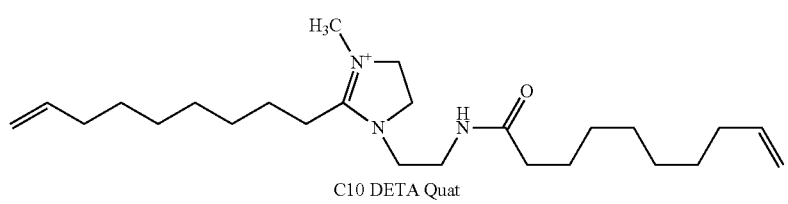
C10 DETA Quat

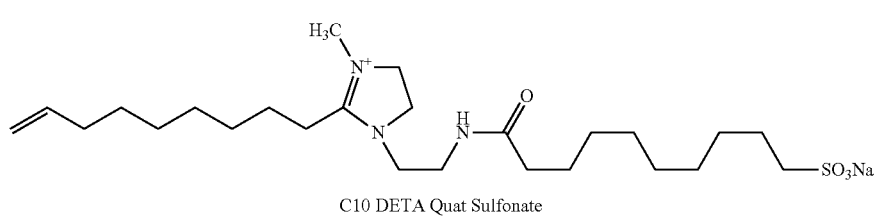
C10 DETA Quat Sulfonate

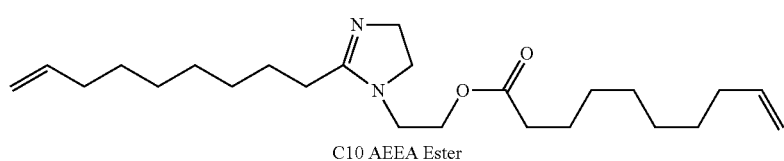
C10 AEEA Ester

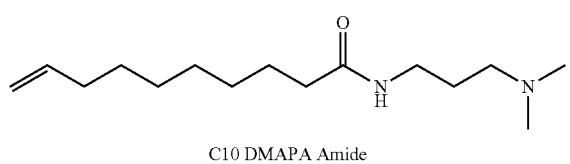
C10 DMAPA Amide

A round-bottom flask equipped with nitrogen sparge tube, mechanical stirrer, and Dean-Stark trap is charged with methyl ester C10-0 (500 g, 2.7 mol), 3-(dimethyl-amino) propylamine ("DMAPA," 331 g, 3.24 mol), and sodium methoxide (8.3 g of a 30% solution of in methanol). The reaction mixture is heated to 100° C. and methanol is collected. The reaction temperature is increased in 5° C. increments until the temperature reaches 130° C. The mixture is held at 130° C. for 1 h, and then a sub-surface nitrogen sparge is applied for 2.5 h. The temperature is elevated to 140° C. for an additional 3.5 h. Collected distillate (122 mL) includes methanol and some DMAPA. The reaction mixture is cooled to 110° C., the nitrogen sparge is discontinued, and vacuum was applied. The mixture is stripped of excess DMAPA (150° C., 20 mm Hg, 30 min.). The product, amidoamine C10-17, has an amine value of 224.14 (eq. wt.: 250.28). $^1$H NMR (CDCl$_3$) confirms formation of the amide, based on disappearance of the methyl ester peak at 3.61 ppm and appearance of the DMAPA CH$_2$ signals at 3.27, 2.09, and 1.60 ppm and the N(CH$_3$)$_2$ at 2.18 ppm.

C10-11

C10-12

C10-13

C10-14

C10-15

C10-17

C10-18

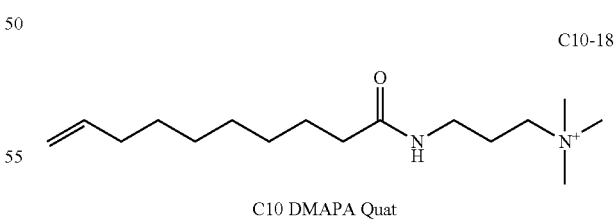
C10 DMAPA Quat

A flask equipped with condenser and nitrogen inlet is charged with amidoamine C10-17 (151.3 g). After warming to 80° C., dimethyl sulfate (68.38 g) is added dropwise. The temperature is raised to 85° C. and the mixture is stirred for 2 h. Isopropyl alcohol (23.45 g) is added, and the mixture stirs for 1 h. The product, C10-18, is analyzed: IPA: 7.72 wt. %; pH: 8.41 (1% in 9:1 IPA/water); iodine value: 56.8; tertiary amine: 0.020 meq/g; moisture: 1.7 wt. %; quaternary actives: 91.2 wt. %.

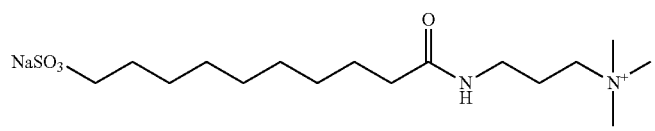
C10 DMAPA Quat Sulfonate — C10-19
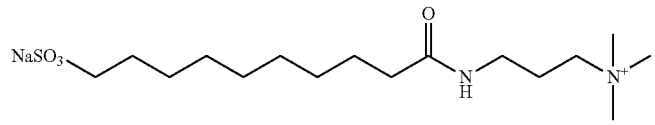
C10 DMAPA AO — C10-20
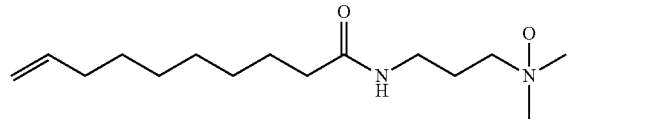
C10 DMAPA AO Sulfonate — C10-21
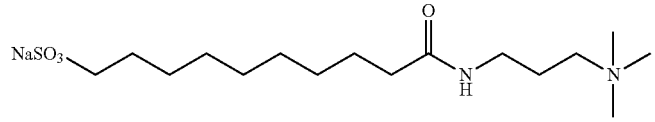
C10 DMAPA Betaine — C10-22
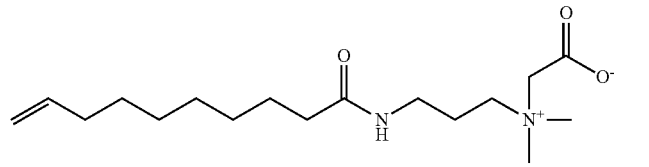
C10 DMAPA Betaine Sulfonate — C10-23
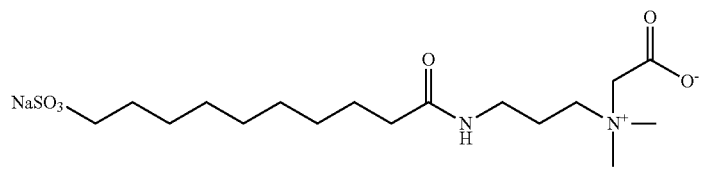
C10 DMAPA Sulfobetaine — C10-24
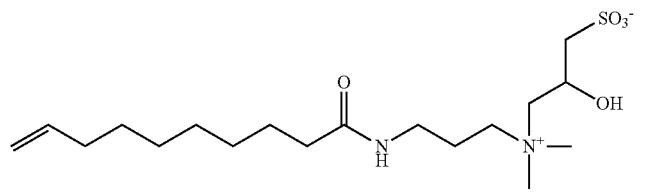
C10 DMA Amide — C10-25
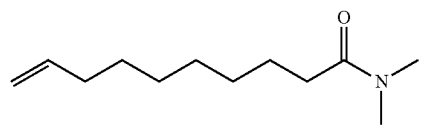
C10 DEA Amide — C10-27
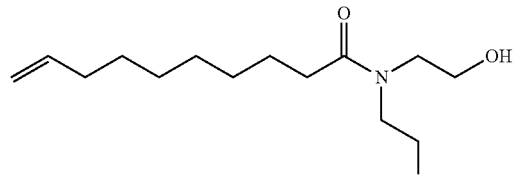

-continued
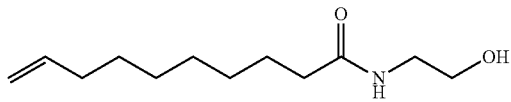
C10 MEA Amide
C10-28
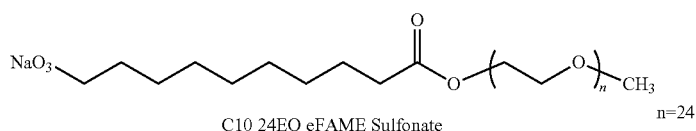
C10 24EO eFAME Sulfonate
C10-30
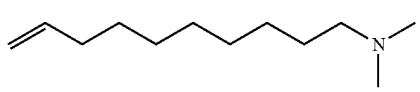
C10 Amine
C10-38
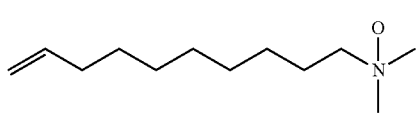
C10 Amine Oxide
C10-39
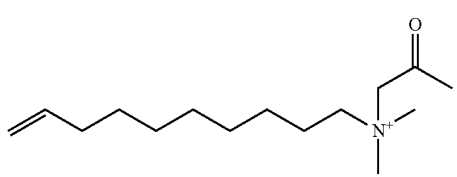
C10 Betaine
C10-41
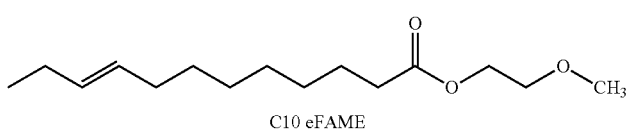
C10 eFAME
C12-8
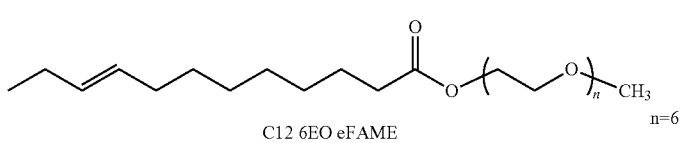
C12 6EO eFAME
C12-9
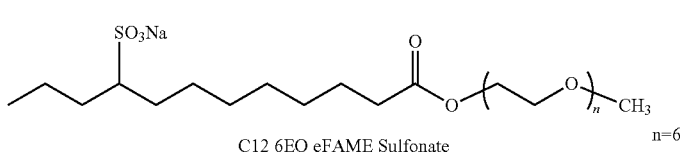
C12 6EO eFAME Sulfonate
C12-10
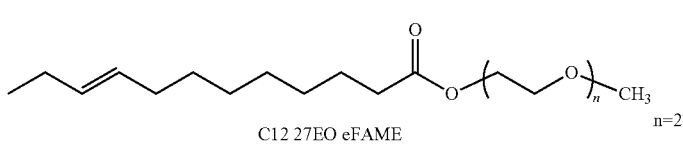
C12 27EO eFAME
C12-11
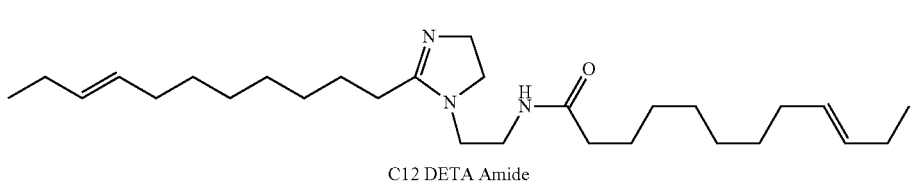
C12 DETA Amide
C12-12

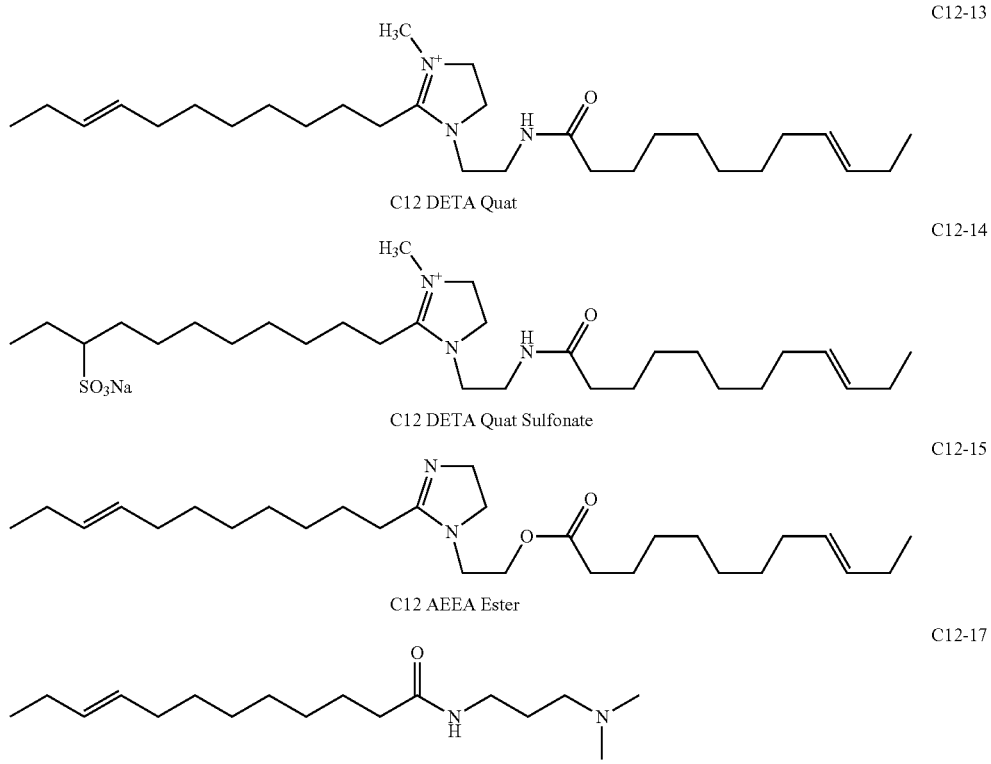

C12-13 C12 DETA Quat

C12-14 C12 DETA Quat Sulfonate

C12-15 C12 AEEA Ester

C12-17

The procedure used to make 010-17 is generally followed with methyl ester C12-0 (670 g), DMAPA (387 g), and sodium methoxide (11.2 g of 30 wt. % solution in methanol). The resulting product, amidoamine C12-17, has an amine value of 196.39 (eq. wt.: 281.3). $^1$H NMR (CDCl$_3$) confirms formation of the amide, based on disappearance of the methyl ester peak at 3.61 ppm and appearance of the DMAPA CH$_2$ signals at 3.30, 2.11, and 1.62 ppm and the N(CH$_3$)$_2$ at 2.20 ppm.

C12-18 C12 DMAPA Quat

A flask equipped with condenser and nitrogen inlet is charged with amidoamine C12-17 (155.8 g), which is warmed to 80° C. Dimethyl sulfate (68.38 g) is added dropwise. The reaction temperature is raised to 85° C. and held for 1 h, then to 95° C. for 3 h. Isopropyl alcohol (24.9 g) is added, and the mixture stirs for 1 h. Analysis of the quat product, C12-18, shows: IPA: 8.9 wt. %; iodine value: 53.95; pH: 8.07 (1% in 9:1 IPA/water); moisture: 0.6 wt. %.

C12-19 C12 DMAPA Quat Sulfonate

C12-20 C12 DMAPA AO

A round-bottom flask is charged with amidoamine C12-17 (250 g), water (400 g), and Hamp-Ex 80 (0.7 g). Dry ice is added until the pH is 8-9. The mixture is heated to 50° C. under nitrogen. Hydrogen peroxide (35 wt. % solution, 88 g) is added dropwise while maintaining the temperature at less than 75° C. The mixture is maintained at 70° C. for 3 h, then cooled to room temperature overnight. The mixture is reheated to 75° C. and water (50 g) is added to help dissolve solids. The mixture is held at 75° C. for 4 h. Analysis with peroxide test strips indicates trace residual peroxide. The mixture is cooled to recover amine oxide C12-20 as an aqueous solution. The product comprises (by titration): 33.4% amine oxide; 0.06% free amine.

C12-22 C12 DMAPA Betaine

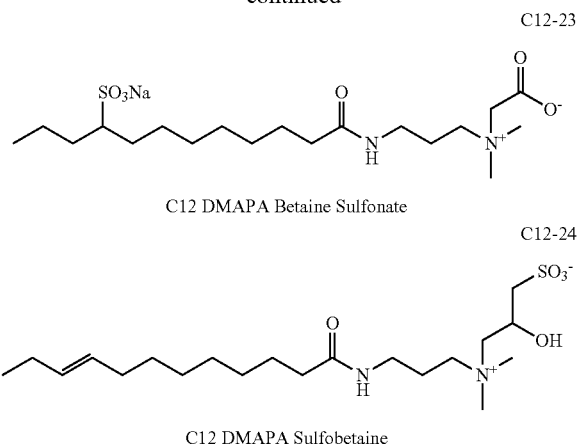

C12 DMAPA Betaine Sulfonate

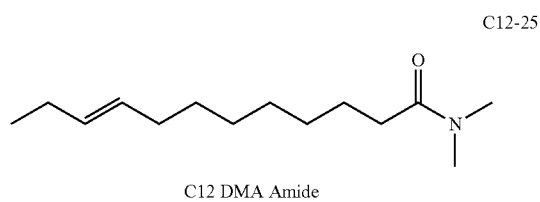 [SMILES: CC/C=C/CCCCCCCC(=O)N(C)C]

C12 DMAPA Sulfobetaine

A flask equipped with nitrogen inlet is charged with sodium metabisulfite (39.6 g) and water (190 g), and the mixture is warmed to 40° C. Aqueous sodium hydroxide (0.6 g of 50% solution) is added. After stirring the mixture 5 min., epichlorohydrin (37.8 g) is added dropwise over 1 h, and the reaction exotherms to 70° C. More aq. NaOH solution (0.6 g) is added and the mixture stirs briefly. Amidoamine C12-17 (105 g) is added, and the temperature is increased to 80° C. for 3.5 h, and the pH (10% aqueous dilution) is kept between 8.2 and 8.6. After 3.5 h, the mixture cools to room temperature overnight. The mixture is reheated to 80° C. After 2 h, the pH is 8.5 and the NaCl level is 6.36%. The reaction is judged complete. The mixture cools to room temperature, and the pH is adjusted to 7.6 with 50% $H_2SO_4$. The sulfobetaine product, C12-24, is analyzed: NaCl: 6.34 wt. %; moisture: 49.7%; solids: 50.4%; sulfobetaine actives (by solids-NaCl): 44.0%. $^1H$ NMR analysis of a dried aliquot of the product mixture supports the proposed structure.

C12-25

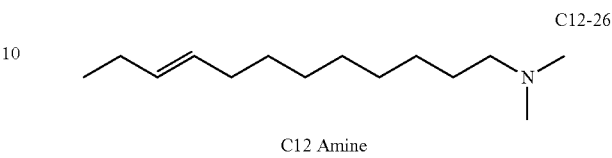

C12 DMA Amide

A round-bottom flask is charged with methyl ester feedstock C12-0 (900.0 g, 4.22 mol) and the material is heated to 60° C. The reactor is sealed and vacuum is applied for 0.5 h to dry/degas the feedstock. The reactor is backfilled with nitrogen, and then sodium methoxide (30 g of 30% solution in methanol) is added via syringe. A static vacuum (–30" Hg) is established, and then dimethylamine ("DMA," 190.3 g, 4.22 mol) is slowly added via sub-surface dip tube. When the pressure equalizes, the reactor is opened to nitrogen overhead and the temperature is increased 70° C. for 1.0 h. The reactor is then cooled to room temperature and the DMA addition is discontinued. Heating resumes to 80° C. and DMA is slowly introduced via sub-surface sparge and held for 2.0 h. The temperature is then increased to 90° C. and held for 1.0 h. $^1H$ NMR spectroscopy indicates >98% conversion. The mixture is cooled to 75° C. and full vacuum is applied to strip methanol and excess DMA. The catalyst is quenched by adding 50% aqueous sulfuric acid (16.3 g) and the mixture is stirred vigorously for 10 min. Deionized water (200 mL) is added and all of the contents are transferred to a bottom-draining vessel. The aqueous layer is removed. The wash is repeated with 300 mL and then 150 mL of deionized water. Approximately 50 mL of 20% NaCl solution is added and the mixture settles overnight. The lower layer is removed and the product is transferred back to the reactor. The product is heated to 75° C. and vacuum is applied to remove residual water. The amide is recovered by vacuum distillation at 120° C. The amide fraction is placed under full vacuum at 135° C. until the ester content is below 1%. Final ester content: 0.7%. Yield: 875 g (91.9%).

C12-26

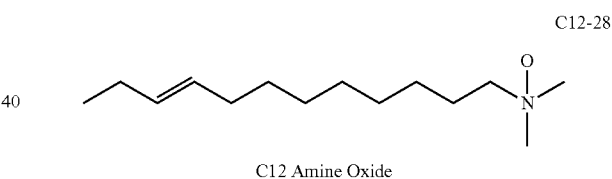

C12 Amine

A nitrogen-blanketed 5-L round-bottom flask is charged with tetrahydrofuran ("THF," 1.5 L) and lithium aluminum hydride pellets ("LAH," 67.8 g, 1.79 mol) and is then cooled in an ice bath. Amide C12-25 (620 g, 2.75 mol) is dissolved in THF (250 mL) and charged to an addition funnel. The amide solution is added dropwise over 3 h to the LAH mixture, keeping the reaction temperature below 15° C. The mixture warms to room temperature and stirs for 16 h. The mixture is cooled with an ice bath and deionized water (68 g) is added dropwise to quench residual LAH. Sodium hydroxide (15%, 68 g) and deionized water (204 g) are added, the reaction mixture warms to room temperature. The mixture is filtered, and solvent is stripped from the resulting filtrate. Phthalic anhydride (50 g) is added to convert a by-product fatty alcohol impurity into its corresponding nonvolatile phthalate ester. The desired amine is isolated from the crude mixture by vacuum distillation, collecting overhead liquid at a pot temperature of 115-120° C. Yield of C12-26: 430.7 g (74%). $^1H$ NMR (CDCl$_3$) confirms the product as pure amine, based on the integration of the N(CH$_3$)$_2$ peak at 2.18 ppm, the olefinic proton signals at 5.2-5.5 ppm, and the terminal methyl group at 0.93 ppm.

C12-28

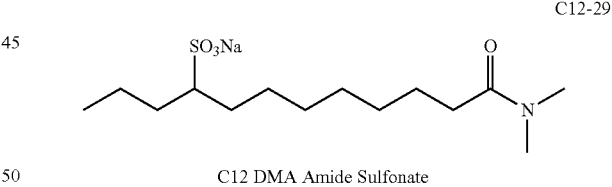

C12 Amine Oxide

C12-29

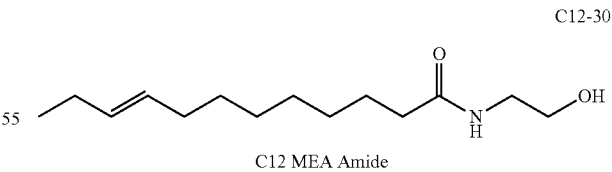

C12 DMA Amide Sulfonate

C12-30

C12 MEA Amide

A round-bottom flask equipped with nitrogen sparge, thermocouple, heating mantle, agitator, and Dean-Stark trap is charged with methyl ester feedstock C12-0 (125.1 g, 0.596 mol) and monoethanolamine (37.2 g, 0.608 mol). The mixture is heated to 60° C. Sodium methoxide (2.14 mL of 30 wt. % solution in methanol, 0.011 mol) is added to the flask, and the reaction exotherms to ~80° C. The mixture is then heated to 100° C. and held for 2.5 h. The reactor is cooled to 90° C. and the Dean-Stark trap is removed. Vacuum is applied incrementally to 20 mm Hg over 0.5 h. Vacuum was held at 20 mm Hg for 0.5 h, then at 1.4 mm Hg for 1.0 h to remove residual methanol. $^1$H NMR spectroscopy indicates complete conversion to the amide. Free MEA, determined by titration, is 0.71%.

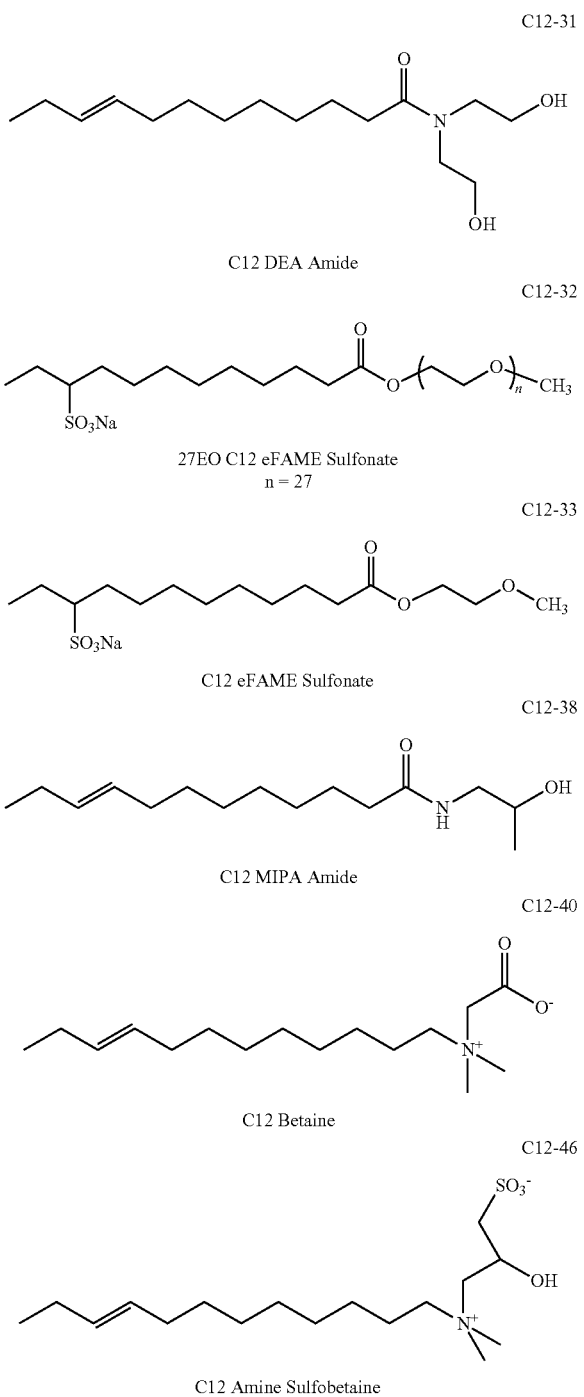

The procedure used to make sulfobetaine C12-24 is generally followed with amine C12-26 (100 g), sodium metabisulfite (48 g), water (203.5 g), 50% aq. NaOH (two 0.6-g portions), and epichlorohydrin (45.9 g). After addition of the tertiary amine, the reaction mixture is heated at 90-95° C. for a total of 10.5 hours while keeping the pH between 7.9 and 8.6 with 50% NaOH (aq) charges (2.3 g, 1 g, and 1 g) and monitoring NaCl level. After 8.5 h, the NaCl level stabilizes well below the expected theoretical value. 3-Chloro-2-hydroxypropanesulfonate, sodium salt hydrate (2.7 g) is added, and the mixture is held at 95° C. for an additional 2 h. The NaCl level stabilizes at 7.24% and the reaction is judged complete and cooled to room temperature. The pH of the product solution is adjusted to 8.1 with a small quantity of 50% $H_2SO_4$. The product, C12-46, is analyzed: pH: 7.53 (10% as is in deionized water); NaCl: 7.82 wt. %; moisture: 48.8 wt. %. $^1$H NMR analysis of a dried aliquot supports the proposed structure (multiplet at ~4.7 for the methine proton, CH—OH).

Evaluation of Light-Duty Liquid Detergents: Mixer Foam Test

This method determines the amount of soil needed to render a dishwashing detergent ineffective as a cleaner. Although the method differs from the large plate method (ASTM D4009-92), it is a similar evaluation. The method involves continuously injecting a known amount of soil sample into a bowl containing warm water and a stirred dish detergent sample. An "end point" is reached at which foam is mostly gone and waves appear at the side of the bowl. Amounts are wt. % unless otherwise indicated.

Soil Preparation:

Each detergent sample is tested using two different soils, which have the following compositions:

1. ASTM D-4009-92, Soil D: Crisco® shortening (42.85%, product of J.M. Smucker Co.), spray-dried egg (14.30%), and warm (40° C.) tap water (42.85%).
2. Shell Soil: Potato powder (15.00%), deionized water (24.80%), formaldehyde (37% aqueous solution, 0.20%), whole milk (30.00%), olive oil (15.00%), and Crisco shortening 15.00%).

Dish Detergent Formulations:

Three different control formulations are used (see below). In each of the test samples, the anionic surfactant is the same as in the control, but the secondary surfactant (the fatty amine oxide in each of the three formulations) is replaced by the test surfactant. The exception is the cationic samples tested (Table 4). These are mixed with sodium lauryl sulfate (SLS) in a 2 (SLS) to 1 (cationic) molar ratio and used to replace the anionic surfactants in the control formulations, while the fatty amine oxides are left the same as in the control formulations. In Control Formulation 1, this blend replaces the sodium alkylbenzene sulfonate and in Control Formulation 2 this blend replaces the sodium lauryl ether sulfate. Control formulations are tested at the beginning of each day of testing.

1. Control Formulation 1 ("C1"): Tap water (97.30%), sodium alkylbenzene sulfonate, linear (2.00% actives), lauryl/myristyl amidopropylamine oxide (0.50 actives), and formaldehyde (0.20%).
2. Control Formulation 2 ("C2"): Tap water (97.30%), sodium lauryl ether sulfate, 2 moles EO (2.00% actives), lauramine oxide (0.50% actives), and formaldehyde (0.20%).
3. Control Formulation 3 ("C3"): Tap water (97.20%), sodium lauryl sulfate (1.50% actives), sodium methyl 2-sulfolaurate and disodium 2-sulfolaurate (0.50 actives), lauryl/myristyl amidopropylamine oxide (0.50% actives), anhydrous magnesium sulfate (0.10%) and formaldehyde (0.20%).

Procedure:

A pre-warmed (50° C. oven) steel mixing bowl is charged with a mixture of warm (52° C.) tap water (495.0 g) and accurately weighed (±0.01 g) detergent formulation (5.0 g). The contents are mixed using a KitchenAid® mixer and whisk attachment at speed setting 6 for 1 min. to build up foam. At the 1 minute mark, soil is dispensed continuously into the stirred mixture using a syringe pump set at 0.40 cm$^3$/min. The amount of foam remaining is monitored, and an end point is noted at which the foam is mostly gone and the test solution makes waves against the side of the bowl. The average amount of soil added (in grams) from duplicate trials is determined for test (F1, F2, F3) and control samples (C1, C2, C3). Results appear in Tables 3, 4, and 5.

instance, the $C_{10}$ DMAPA amide C10-17 performs well in the test, while the $C_{12}$ analog, C12-17 gives inferior performance.

TABLE 3

Performance as Secondary Surfactant in a Light-Duty Liquid Dish Detergent
Amount of Soil Mixture Needed to De-Foam (g)
Inventive Examples: Overall Performance Equals or Exceeds Control

| | Shell Soil | | | | | | ASTM D4009 Soil D | | | | | |
|---|---|---|---|---|---|---|---|---|---|---|---|---|
| sample | F1 | C1 | F2 | C2 | F3 | C3 | F1 | C1 | F2 | C2 | F3 | C3 |
| C10-17 | 2.32 | 3.98 | 3.42 | 3.76 | 2.88 | 3.05 | 1.20 | 2.20 | 1.55 | 2.03 | 1.42 | 1.70 |
| C12-20 | 3.18 | 3.52 | 2.78 | 3.55 | 2.48 | 2.94 | 1.28 | 1.39 | 1.09 | 1.57 | 1.05 | 1.46 |
| C12-24 | 3.36 | 3.52 | 2.58 | 3.55 | 2.07 | 2.94 | 1.24 | 1.39 | 1.16 | 1.57 | 1.06 | 1.46 |
| C12-30 | 1.80 | 3.36 | 3.12 | 3.40 | 2.59 | 2.89 | 0.87 | 1.52 | 1.39 | 1.77 | 1.08 | 1.58 |
| C12-38* | 1.93 | 3.36 | 2.72 | 3.40 | 2.37 | 2.89 | 1.08 | 1.52 | 1.20 | 1.77 | 0.91 | 1.58 |
| C12-46 | 3.53 | 4.50 | 3.79 | 3.44 | 3.20 | 3.78 | 1.05 | 1.56 | 1.23 | 1.88 | 1.26 | 1.67 |

*Although amide C12-38 does not equal or exceed the performance of the amine oxide controls shown here, it does perform as well as or better than cocamide DEA, a typical amide used in economy LDL formulations.

TABLE 4

Performance as Primary Surfactant in a Light-Duty Liquid Dish Detergent
Cationic Samples
Amount of Soil Mixture Needed to De-Foam (g)
Inventive Examples: Overall Performance Equals or Exceeds Control

| | Shell Soil | | | | | | ASTM D4009 Soil D | | | | | |
|---|---|---|---|---|---|---|---|---|---|---|---|---|
| sample | F1 | C1 | F2 | C2 | F3 | C3 | F1 | C1 | F2 | C2 | F3 | C3 |
| C10-18 | 5.40 | 3.92 | 3.49 | 3.95 | — | — | 2.97 | 1.85 | 1.70 | 1.82 | — | — |
| C12-18 | 4.48 | 3.92 | 3.78 | 3.95 | — | — | 2.04 | 1.41 | 2.04 | 1.82 | — | — |

As the results demonstrate, it is not easy to predict which classes of compounds will provide at least good performance when tested as a replacement for a conventional secondary surfactant in a light-duty liquid detergent formulation. For Conversely, the $C_{12}$ compounds C12-20 (DMAPA amine oxide) and C12-24 (DMAPA sulfobetaine) perform well in the test, while the $C_{10}$ analogs C10-20 and C10-24 perform poorly.

TABLE 5

Performance as Secondary Surfactant in a Light-Duty Liquid Dish Detergent
Amount of Soil Mixture Needed to De-Foam (g)
Comparative Examples: Overall Performance Inferior to Control

| | Shell Soil | | | | | | ASTM D4009 Soil D | | | | | |
|---|---|---|---|---|---|---|---|---|---|---|---|---|
| sample | F1 | C1 | F2 | C2 | F3 | C3 | F1 | C1 | F2 | C2 | F3 | C3 |
| C10-11 | 1.24 | 3.13 | 2.28 | 3.45 | 1.40 | 2.80 | 0.59 | 1.68 | 0.81 | 2.11 | 0.65 | 1.68 |
| C10-12 | 0.06 | 3.13 | 2.16 | 3.84 | 0.14 | 2.86 | 0.05 | 1.68 | 0.75 | 2.03 | 0.30 | 1.68 |
| C10-13 | 0.32 | 3.13 | 2.51 | 3.45 | 1.53 | 2.80 | 0.10 | 1.68 | 0.99 | 2.11 | 0.59 | 1.76 |
| C10-14 | 0.68 | 3.55 | 2.43 | 3.45 | 1.23 | 3.18 | 0.35 | 1.67 | 0.85 | 1.91 | 0.51 | 1.76 |
| C10-15 | 0.07 | 3.13 | 1.41 | 3.86 | 0.71 | 2.86 | 0.13 | 1.68 | 0.75 | 2.03 | 0.48 | 1.68 |
| C10-19 | 0.86 | 3.39 | 1.85 | 3.84 | 0.90 | 2.86 | 0.42 | 1.32 | 0.88 | 2.25 | 0.61 | 1.80 |
| C10-20 | 1.92 | 3.98 | 2.64 | 4.15 | 1.56 | 3.05 | 0.69 | 2.20 | 1.16 | 2.03 | 0.71 | 1.70 |
| C10-21 | 0.81 | 3.52 | 2.18 | 3.54 | 0.97 | 2.94 | 0.50 | 1.53 | 0.86 | 1.90 | 0.50 | 1.46 |
| C10-22 | 1.46 | 3.99 | 2.69 | 4.15 | 1.61 | 3.05 | 0.94 | 2.20 | 1.16 | 2.03 | 0.79 | 1.70 |
| C10-23 | 1.03 | 3.43 | 2.04 | 3.56 | — | — | 0.53 | 1.60 | 0.89 | 1.87 | — | — |
| C10-24 | 2.39 | 3.43 | 2.39 | 3.56 | 1.62 | 3.00 | 0.94 | 1.60 | 0.92 | 1.87 | 0.71 | 1.42 |
| C10-25 | 1.56 | 3.99 | 2.58 | 4.15 | 1.93 | 3.05 | 0.72 | 1.90 | 1.10 | 1.87 | 0.93 | 1.70 |
| C10-27 | 1.20 | 3.36 | 2.69 | 3.54 | 1.18 | 2.89 | 0.57 | 1.52 | 1.00 | 1.90 | 0.57 | 1.58 |
| C10-28 | 1.36 | 3.39 | 2.27 | 3.84 | 1.22 | 2.99 | 0.53 | 1.32 | 0.94 | 2.25 | 0.82 | 1.80 |
| C10-30 | 0.74 | 3.55 | 1.89 | 3.45 | 1.08 | 3.18 | 0.50 | 1.67 | 0.88 | 1.91 | 0.49 | 1.76 |
| C10-38 | 0.99 | 3.55 | 3.02 | 3.79 | 2.81 | 3.18 | 0.33 | 1.67 | 1.29 | 1.91 | 1.45 | 1.76 |
| C10-39 | 1.07 | 3.55 | 2.32 | 3.79 | 1.31 | 3.18 | 0.59 | 1.67 | 0.99 | 1.91 | 0.65 | 1.76 |
| C10-41 | 0.47 | 3.55 | 2.42 | 3.79 | 2.01 | 3.18 | 0.61 | 1.67 | 1.15 | 1.91 | 1.00 | 1.76 |
| C12-8 | 0.38 | 3.39 | 2.62 | 3.84 | 1.73 | 2.86 | 0.25 | 1.72 | 0.92 | 2.25 | 0.71 | 1.80 |
| C12-9 | 2.64 | 3.39 | 1.86 | 3.84 | 1.40 | 2.86 | 0.50 | 1.72 | 0.79 | 2.03 | 0.85 | 1.80 |
| C12-10 | 1.32 | 3.52 | 2.09 | 3.40 | 1.41 | 3.20 | 0.64 | 1.67 | 0.79 | 1.97 | 0.63 | 1.76 |
| C12-11 | 2.51 | 3.13 | 2.00 | 3.86 | 1.59 | 2.86 | 0.78 | 1.68 | 0.92 | 2.03 | 0.68 | 1.68 |

TABLE 5-continued

Performance as Secondary Surfactant in a Light-Duty Liquid Dish Detergent
Amount of Soil Mixture Needed to De-Foam (g)
Comparative Examples: Overall Performance Inferior to Control

| sample | Shell Soil | | | | | | ASTM D4009 Soil D | | | | | |
|---|---|---|---|---|---|---|---|---|---|---|---|---|
| | F1 | C1 | F2 | C2 | F3 | C3 | F1 | C1 | F2 | C2 | F3 | C3 |
| C12-12 | 0.17 | 3.39 | 1.40 | 3.86 | 0.00 | 2.99 | 0.06 | 1.32 | 0.39 | 2.25 | 0.00 | 1.80 |
| C12-13 | 0.21 | 3.79 | 1.42 | 3.75 | 0.34 | 3.38 | 0.10 | 1.65 | 0.49 | 2.00 | 0.21 | 1.79 |
| C12-14 | 0.58 | 3.13 | 2.30 | 3.45 | 1.24 | 2.80 | 0.44 | 1.68 | 0.81 | 1.91 | 0.56 | 1.76 |
| C12-15 | 0.13 | 3.13 | 1.50 | 3.45 | 0.42 | 2.86 | 0.05 | 1.86 | 0.54 | 2.03 | 0.29 | 1.68 |
| C12-17 | 1.49 | 3.99 | 3.36 | 4.15 | — | — | 0.79 | 1.90 | 1.45 | 1.87 | — | — |
| C12-19 | 0.90 | 3.13 | 2.20 | 3.45 | 1.29 | 2.80 | 0.43 | 1.68 | 1.03 | 2.03 | 0.85 | 1.68 |
| C12-22 | 1.85 | 3.43 | 2.77 | 3.56 | 2.52 | 3.00 | 0.93 | 1.60 | 1.29 | 1.87 | 1.13 | 1.42 |
| C12-23 | 0.84 | 3.36 | 2.38 | 3.54 | 1.45 | 2.89 | 0.49 | 1.54 | 0.87 | 1.77 | 0.63 | 1.58 |
| C12-25 | 1.09 | 3.13 | 2.52 | 3.45 | 2.42 | 2.80 | 0.57 | 1.68 | 1.16 | 2.11 | 1.02 | 1.76 |
| C12-26 | 0.15 | 3.55 | 2.50 | 3.79 | 1.56 | 3.18 | 0.15 | 1.67 | 1.20 | 2.09 | 0.80 | 1.76 |
| C12-28 | 1.19 | 3.55 | 2.37 | 3.79 | 2.81 | 3.18 | 0.57 | 1.67 | 1.32 | 2.09 | 1.42 | 1.76 |
| C12-29 | 0.83 | 3.55 | 2.16 | 3.40 | 1.08 | 3.18 | 0.59 | 1.67 | 0.78 | 1.97 | 0.54 | 1.76 |
| C12-31 | 1.81 | 3.39 | 2.82 | 3.84 | 2.10 | 2.99 | 0.80 | 1.32 | 1.17 | 2.25 | 0.99 | 1.80 |
| C12-32 | 1.01 | 3.55 | 2.21 | 3.40 | 1.02 | 3.18 | 0.47 | 1.67 | 0.85 | 1.97 | 0.48 | 1.76 |
| C12-33 | 0.83 | 3.52 | 2.06 | 3.40 | 1.23 | 3.20 | 0.53 | 1.61 | 0.78 | 1.97 | 0.55 | 1.80 |
| C12-40 | 0.36 | 3.52 | 3.01 | 3.40 | 1.83 | 3.20 | 0.37 | 1.61 | 1.38 | 1.97 | 0.82 | 1.80 |

The preceding examples are meant only as illustrations. The following claims define the invention.

We claim:

1. A light-duty liquid detergent comprising water, 0.1 to 30 wt. % of at least one anionic surfactant selected from the group consisting of fatty alkyl sulfates, fatty alkyl ether sulfates, alkyl aryl sulfonates, and fatty ester sulfonates, and 0.1 to 10 wt. % of at least one secondary surfactant derived from a metathesis-derived $C_{10}$-$C_{17}$ monounsaturated acid or its ester derivatives and selected from the group consisting of $C_{10}$ amidoamines, quaternized $C_{10}$ or $C_{12}$ amidoamines, $C_{12}$ amidoamine oxides, $C_{12}$ sulfobetaines, $C_{12}$ amidoamine sulfobetaines, and $C_{12}$ alkanolamides;

wherein the $C_{10}$ amidoamine has the structure:

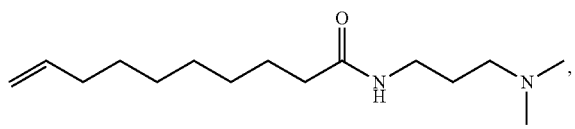 [SMILES: C=CCCCCCCCC(=O)NCCCN(C)C]

the quaternized $C_{10}$ or $C_{12}$ amidoamine has the structure:

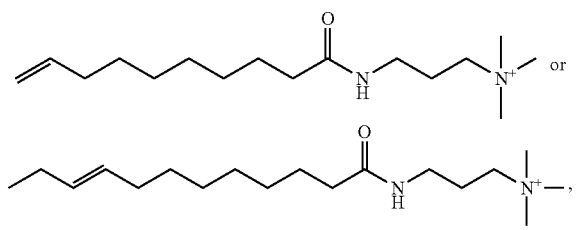

the $C_{12}$ amidoamine oxide has the structure:

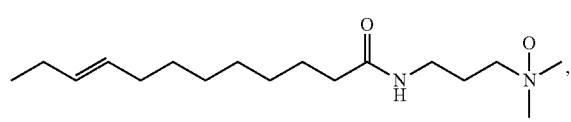

the $C_{12}$ sulfobetaine has the structure:

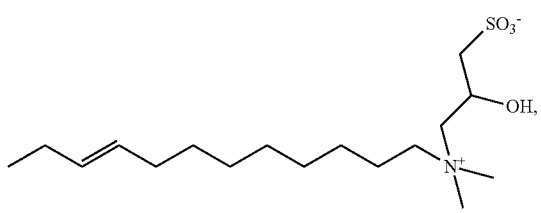

the $C_{12}$ amidoamine sulfobetaine has the structure:

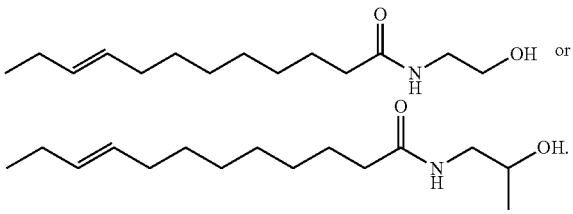

and the $C_{12}$ alkanolamide has the structure:

2. The detergent of claim 1 wherein the secondary surfactant is a $C_{10}$ amidoamine having the structure:

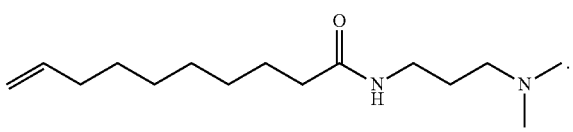 [SMILES: C=CCCCCCCCC(=O)NCCCN(C)C]

3. The detergent of claim 1 wherein the secondary surfactant is a quaternized $C_{10}$ or $C_{12}$ amidoamine having the structure:

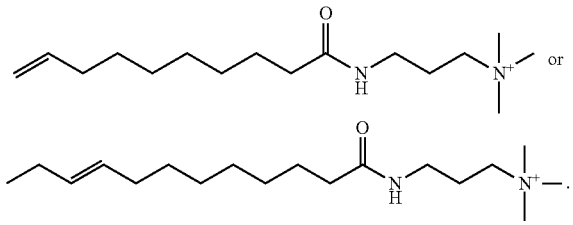

4. The detergent of claim 1 wherein the secondary surfactant is a $C_{12}$ amidoamine oxide having the structure:

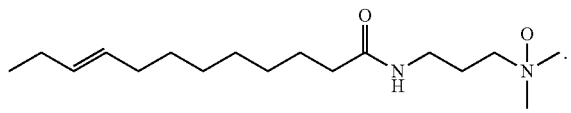

5. The detergent of claim 1 wherein the secondary surfactant is a $C_{12}$ sulfobetaine having the structure:

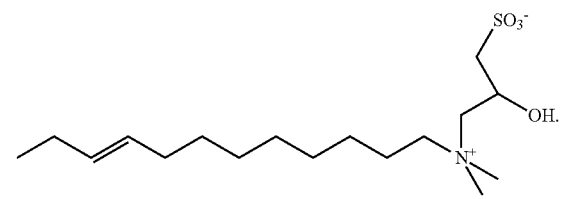

6. The detergent of claim 1 wherein the secondary surfactant is a $C_{12}$ amidoamine sulfobetaine having the structure:

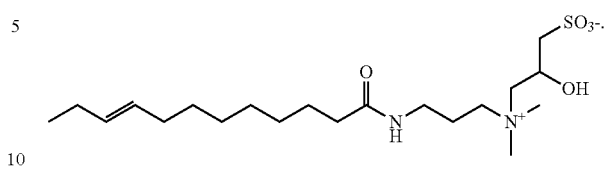

7. The detergent of claim 1 wherein the secondary surfactant is a $C_{12}$ alkanolamide having the structure:

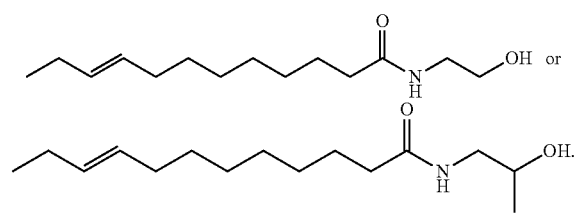

8. The detergent of claim 1 wherein the acid or ester derivative reactant has at least 1 mole % of trans-$\Delta^9$ unsaturation.

9. The detergent of claim 1 comprising from 0.2 to 8 wt. % of the secondary surfactant.

10. The detergent of claim 1 further comprising one or more additives selected from the group consisting builders, buffers, abrasives, electrolytes, diamines, bleaching agents, fragrances, dyes, foaming control agents, foam enhancers, polymeric suds stabilizers, antimicrobial agents, thickeners, pigments, gloss enhancers, enzymes, dispersants, hydrotropes, opacifiers, chelants, preservatives, UV light absorbers, color stabilizers, vitamins, herbal extracts, emollients, skin conditioners, humectants, rheology modifiers, solvents, surfactants, and pearlescent agents.

\* \* \* \* \*